United States Patent [19]    [11] Patent Number: 4,980,291
Bianchi et al.                                [45] Date of Patent: Dec. 25, 1990

[54] PROCESS FOR THE ENZYMATIC SEPARATION OF THE OPTICAL ISOMERS OF RACEMIC ALPHA-ALKYL-SUBSTITUTED PRIMARY ALCOHOLS

[75] Inventors: Daniele Bianchi, Milan; Pietro Cesti, Trecate; Franco Francalanci, Novara; Walter Cabri, Limbiate, all of Italy

[73] Assignee: Istituto Guido Donegani S.p.A., Novara, Italy

[21] Appl. No.: 307,913

[22] Filed: Feb. 9, 1989

[30]     Foreign Application Priority Data

Feb. 10, 1988 [IT] Italy ............................ 19361 A/88

[51] Int. Cl.$^5$ ............................................. C12P 7/22
[52] U.S. Cl. .................................... 435/280; 435/155; 435/156; 435/157
[58] Field of Search ............... 435/280, 155, 156, 157

[56]            References Cited
                    PUBLICATIONS

Kirchner et al., J. Am. Chem. Soc. vol. 107 (1985) pp. 7072–7076.
Cambou et al.,-J. Am. Chem. Soc. vol. 106 (1984) pp. 2687–2692.

*Primary Examiner*—Sam Rosen
*Attorney, Agent, or Firm*—Morgan & Finnegan

[57]            ABSTRACT

Biotechnological resolution by means of enzymatic transesterification of the relevant racemic mixture of the optical isomers of α-alkyl-substituted primary alcohols having the formula (I):

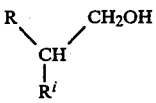

(I)

wherein:
R represents a linear or branched ($C_1$–$C_{20}$)-alkyl or alkenyl group or an aryl group, also substituted or condensed with other groups, in particular a group of formula (II) or (III):

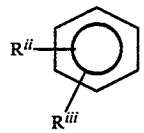

(II)

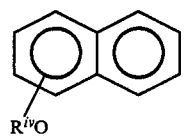

(III)

wherein:
$R^{ii}$ represents a ($C_1$–$C_8$)-alkyl group, a ($C_1$–$C_4$)-alkenyl group, an alkoxy, phenyl, phenoxy, benzoyl, or heterocyclic group;
$R^{iii}$ represents a hydrogen or halogen atom;
$R^{iv}$ represents a ($C_1$–$C_4$)-alkyl group,
and wherein
$R^i$ represents a ($C_1$–$C_4$)-alkyl group either equal to, or different from, R, in the presence of an enzyme either free or immobilized on a support capable of selectively causing the S isomer to be esterified, with the R isomer being left substantially unchanged, said isomers being then separated according to techniques known from the prior art. The process is used in the synthesis of antiinflammatory agents.

8 Claims, No Drawings

PROCESS FOR THE ENZYMATIC SEPARATION OF THE OPTICAL ISOMERS OF RACEMIC ALPHA-ALKYL-SUBSTITUTED PRIMARY ALCOHOLS

DESCRIPTION OF THE INVENTION

The present invention relates to a process for the enzymatic separation of the optical isomers of racemic α-alkyl-substituted primary alcohols.

More particularly, the present invention relates to a biotechnological process for carrying out the separation, or resolution, of the optical isomers of α-alkyl-substituted primary alcohols having the formula (I):

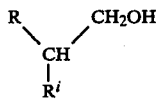

wherein:
R represents a linear or branched $(C_1-C_{20})$-alkyl or alkenyl group or an aryl group, also substituted or condensed with other groups, in particular a group of formula (II) or (III):

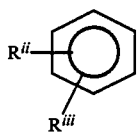

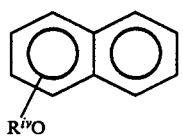

wherein:
$R^{ii}$ represents a $(C_1-C_8)$-alkyl group, a $(C_1-C_4)$-alkenyl group, an alkoxy, phenyl, phenoxy, benzoyl or heterocyclic group;
$R^{iii}$ represents a hydrogen or halogen atom;
$R^{iv}$ represents a $(C_1-C_4)$-alkyl group,
and wherein
$R^i$ represents a $(C_1-C_4)$-alkyl group either equal to, or different from, R,
which usually exist as a mixture of optical isomers, which process is carried out in the presence of enzymes performing an esterasic activity, either free or immobilized on a support, derived from microorganisms or animal tissues which enzymes are capable of causing the S isomer to be selectively esterified, with the R isomer being left substantially unchanged.

Such alcohols, as enantiomers, or pure optical isomers, may be used as intermediates in the synthesis of α-alkyl-substituted carboxy-acids, used as non-steroidal antiinflammatory agents (e.g., Naproxen, Ibuprofen).

A method for separating the optical antipodes of the alcohols of formula (I) by enzymatic esterification is disclosed by the Author Sonnet (J. Org. Chem. 52, 3477-3479).

However, such a method makes it possible for the compounds of formula (I) to be obtained only at a low degree of optical purity, and therefore it is not applicable at an industrial level.

Therefore the need existed of having available a method which would make possible the resolution of the optical isomers of α-alkyl-substituted primary alcohols having formula (I) to be carried out in a simple, efficient and cheap way.

An object of the present invention is that of carrying out the separation of the optical isomers of racemic α-alkyl-substituted alcohols of formula (I) in a simple, efficacious and cheap way, with a high degree of optical purity.

In accordance with the present invention it has now been discovered that this purpose is accomplished by means of a biotechnological process for the enzymatic asymmetrical esterification of the racemic compounds of formula (I), with the use of a particular class of enzymes, more fully defined in the following:

In practice, an enzyme belonging to the classes of the Lipases is used, which is capable of causing the reaction of esterification to take place stereoselectively on the (S) isomer of the racemic alcohol (I), while leaving the (R) isomer substantially unaltered.

Therefore, the principal object of the present invention is a process for the enzymatic separation of the optical isomers of the racemic α-alkyl-substituted primary alcohols, having the above defined formula (I), consisting or consisting essentially in reacting compounds of formula:

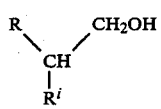

wherein: R and $R^i$ have the above defined meanings, with an ester having the formula (IV):

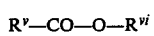

wherein
$R^v$ and $R^{vi}$, which may be equal to or different from each other, represent $(C_1-C_8)$-alkyl groups,
at temperatures within the range from 0° to 60° C., in the presence of an either free or immobilized enzyme capable of causing the (S) isomer to be selectively esterified, with the (R) isomer of the racemic starting compound of formula (I) being left substantially unchanged.

The ester thus produced in the (S) configuration, and the alcohol in the (R) configuration may be then separated by substantially operating according to traditional techniques. The racemic α-alkyl-substituted alcohols of formula (I) used as the starting compounds, are per se known, and/or can be synthesized according to conventional techniques.

According to a schematic representation of the process according to the present invention, the racemic alcohols of formula (I) are reacted, in the presence of an enzyme, with an ester of carboxy acid of formula (IV) according to the reaction:

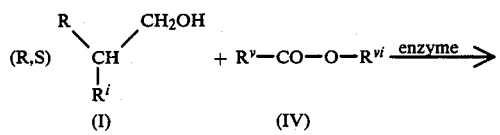

-continued

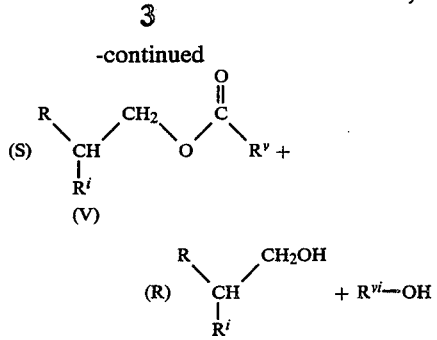

wherein the symbols R, $R^i$, $R^v$, $R^{vi}$ have the above defined meanings.

Preferred esters of formula (IV) are: ethyl acetate, methyl propionate, methyl acetate, and so forth.

The ester of the carboxy acid (IV) is used in excess, in that in the reaction it is used both as a reactant and as the solvent. More particularly, molar ratios of the ester (IV) to the alcohol (I) are used which are within the range of from 10:1 to 500:1, and preferably are within the range of from 20:1 to about 100:1.

The enzyme is used in an amount corresponding to a weight ratio of the enzyme to the substrate of formula (I) within the range of from 1:1 to about 1:1000.

The transesterification process is carried out by vigorously stirring the reaction mixture constituted by the reactant (I) and the ester (IV), which acts both as the reactant and as the solvent, and by the either free or supported enzyme as disclosed in greater detail in the following, at temperatures comprised within the range of from 0° to 60° C., and preferably from 20° to about 30° C.

At the end of the reaction the solid phase is filtered off; said solid phase is essentially constituted by the enzyme, which can be recovered and used again, without any substantial loss in activity.

From the filtrate constituted by the organic reaction phase, the alcohol (I) in the (R) configuration, and the ester (V) in the (S) configuration are separated by using such traditional methods as column chromatography, or the fractional distillation.

The ester (V) in (B) configuration may subsequently be subjected to an alkaline hydrolysis, in order to yield the (S) isomer of alcohol (I).

The enzymes used according to the present invention belong to the class of the lipases, and can be of either animal or microbial origin.

In particular, Steapsin (from pig pancreas, marketed by Sigma Chem. Co., U.S.A.) and Lipase P (from *Pseudomonas fluorescens*, marketed by Amano Pharm. Co., Japan) have been shown to be active.

According to the present invention, the enzymes may be used either free or immobilized on suitable supports in order to increase their activity, their stability and to facilitate their recovery and re-use.

Porous supports having a high surface area, such as, e.g., celite, porous glass, silica, and so forth, have shown to be particularly suitable for the intended purpose.

The immobilization may be easily carried out by causing a buffered aqueous solution of the enzyme to be absorbed on the support, and then removing to dryness the solvent from the thus-impregnated support.

The process, thanks to its simple and mild operating conditions, is particularly advantageous. A particularly highly interesting aspect thereof is constituted by the possibility of operating according to a single-step process, which leads to the direct separation of the desired (S) form from the (R) isomer, with high yields and high purity levels.

The invention will now be further illustrated by means of the following examples, supplied for merely illustrative and non-limitative, purposes:

EXAMPLE 1

Separation of the Enantiomers of 2-(6-Methoxy-2-Naphthyl)-Propan-1-ol

To 1 g of (R,S)-2-(6-methoxy-2-naphthyl)-propan-1-ol dissolved in 40 ml of ethyl acetate, 250 mg of lyophilized Steapsin (marketed by Sigma Chemical Co., U.S.A.) is added.

The mixture is vigorously stirred at a temperature of 20° C., and the reaction is monitored by gas-chromatography.

After 96 hours (conversion of 43%), the enzyme is recovered by filtration, and ethyl acetate is evaporated under reduced pressure.

The residue is then chromatographed on a silica gel column, with a 95−5 volume/volume (V/V) hexane-ether blend being used as the eluent.

In that way the following are obtained: 500 mg of (S) 2-(6-methoxy-2-naphthyl)-1-acetoxy-propane, as a white solid with $[\alpha]_D^{20} -13.6°$ (C=1, benzene), ee 95%, H-NMR (90 MHz in $COCl_3$)δ(ppm): 1.4 (3M, s, $CHCH_3$); 2.0 (3H, s, $COCH_3$); 3.0–3.4 (1H, m, $CHH_3$); 3.8 (3H, s, $OCH_3$); 4.2 (2M, d, $CH_2O$); 7.0–7.7 (6H̄, m, aromatics); and 540 mg of (R)-2-(6-methoxy-2-naphthyl)-propan-1-ol, as a white solid with $[\alpha]_D^{20} +12.2°$ (C=1, $CHCl_3$), ee 67%, H-NMR (90 MHz in COCl)δ(ppm): 1.4 (3H, d, CHCHHD 3); 2.9–3.4 (1H, m, $CHH_3$), 3.7 (2H, d, $CH_2O$); 3.8 (3H, s, $OCH_3$); 7.0–7.8 (6H̄, m, aromatics).

EXAMPLES 2–7

By using the same procedure as disclosed above in Example 1, and using ethyl acetate or methyl propionate as the solvents, the enantiomers of 2-methyl-butan-1-ol, 2-ethylhexan-1-ol, 2-phenyl-propan-1-ol, 2-(4-isobutyl-phenyl)propan-1-ol and 2-(6-methoxy-2-naphthyl)-propan-1-ol were separated.

The results thus obtained are reported in Table 1.

EXAMPLE 8

Immobilization of Steapsin on Célite

To 1 g of Celite 577 (marketed by Johns Manville Ltd. Richmond, Surrey, U.K.), 250 mg of enzyme Steapsin dissolved in 5 ml of 0.1 N Na/K phosphate buffer, pH 7, is added The so-obtained mixture is mixed, so as to obtain a homogeneous distribution of the enzyme, and is then dried in air at 20° C. for 18 hours.

Separation of the Enantiomers of 2-(4-Isobutyl-Phenyl)-Propan-1-ol

To 1 g of (R,S)-2(4-isobutyl-phenyl)-propan-1-ol dissolved in 40 ml of ethyl acetate 80 mg of Steapsin immobilized on 320 mg of Celite 577 as hereinabove disclosed, is added.

The mixture is vigorously stirred at a temperature of 20° C., and the reaction is monitored by gas-chromatography.

After 48 hours (conversion of 50%), the supported enzyme is recovered by filtration, and ethyl acetate is evaporated under reduced pressure.

The residue is chromatographed on a silica gel column, with a 95−5 V/V hexane-ethyl ether blend being used as the eluent.

The following are obtained: 590 mg of (S)-2-(4- isobutyl-phenyl)-1-acetoxy-propane, as a colorless oil with $[\alpha]_D^{20} -7.0°$ (C=1, benzene), ee 98%, H-NMR (90 MHz in COCl$_3$) (ppm): 0.9 (6H, d, C$\underline{H}$HD 3CHC$\underline{H}$HD 3); 1.3 (3H, d, C$\underline{H}$HD 3CH); 1.5–2.0 (1$\overline{H}$, m, CH$_3$C$\overline{H}$H$_3$); 2.1 (3H, s, COC$\underline{H}$$_3$; 2.4 (2H, d, C$_6$H$_4$C$\underline{H}$HD 2); 3.1–2.7 (1H, m, C$_6$H$_4$C$\underline{H}$HD 2); 4.1 (2H, d, C$\underline{H}$$_2$O); 7.0 (4H, s, aromatics); and 490 mg of (R)-2-(4-isopropyl-phenyl)-propan-1-ol as a colorless oil with $[\alpha]_D^{20}+12.8°$ (C=1, CHCl$_3$), ee 97%, H-NMR (90 MHz in COCl$_3$)δ(ppm): 0.9 (6H, d, C$\underline{H}$HD 3CHC$\underline{H}$HD 3); 1.3 (3H, d, C$\underline{H}$HD 3CH), 1.7–2.2 (1H, m.$^-$CH$_3$C$\underline{H}$H$_3$); 2.5 (2$\overline{H}$, d, C$_6$H$_4$CH$_2$); 2.7–3.2 (1H, m, C$_6$$\overline{H}$$_4$CH); 3.7 (2H, d, CH$_2$O); 7.0 (4H, s, C$_6$H$_4$).

EXAMPLES 9–13

By using the same procedure as disclosed in Example 8, and using ethyl acetate or methyl propionate as solvents, the enantiomers of 2-methyl-butan-1-ol, 2-ethyl-hexan-1-ol, 2-phenyl-propan-1-ol, 2-(4-isobutyl-phenyl)-propan-1-ol and 2-(6-methoxy-2-naphthyl)-propan-1-ol were separated.

The results obtained are reported in Table 2.

EXAMPLE 14

Separation of the Enantiomers of 2-Ethyl-Hexan-1-ol

To 1 g of (R,S)-2-ethyl-hexan-1-ol dissolved in 40 ml of ethyl acetate, 40 mg of Lipase Amano P (marketed by Amano Pharm. Co., Japan) immobilized on 160 mg of Celite 577, as disclosed in Example 8 for Steapsin, is added.

The mixture is vigorously stirred at a temperature of 20° C., and the reaction is monitored by gas-chromatography.

After 24 hours (conversion of 50%), the supported enzyme is recovered by filtration, and ethyl acetate evaporated under reduced pressure.

The residue is then chromatographed on a silica gel column, with a 95−5 V/V hexane-ethyl ether blend being used as the eluent.

The following are obtained: 620 mg of 2-ethyl-1-acetoxy-hexane as a colorless oil with $[\alpha]_D^{20}+2.3°$ (as such), ee 96%, H-NMR (90 MHz in COCl$_3$)δ(ppm): 1.0–1.5 (14H, m, CH$_3$CH$_2$CH$_2$CH$_2$CHCH$_2$CH$_3$); 2.0 (3H, s, COCH$_3$); 4.0 (2H, d, CH$_2$O); and 470 mg of 2-ethyl-hexan-1-ol, as a colorless oil with $[\alpha]_D^{20}-1.52°$ (as such), ee 96%.

EXAMPLES 15–18

By using the same procedure as disclosed in Example 14, and using ethyl acetate or methyl propionate as solvents, the enantiomers of 2-methyl-butan-1-ol, 2-ethyl-hexan-1-ol, 2-phenyl-propan-1-ol and 2-(6-methoxy-2-naphthyl)-propan-1-ol were separated.

The results obtained are reported in Table 3.

TABLE 1

| Example | Substrate | Solvent | Time (h) | Conversion (%) | (R) Alcohol $[\alpha]_D^{20}$ | Recovery ⊖⊕ | (S) Ester $[\alpha]_D^{20}$ | Product ⊖⊕ |
| --- | --- | --- | --- | --- | --- | --- | --- | --- |
| 2 | | Ethyl acetate | 48 | 48 | +5.3 (a) | 91 | +4.3 (b) | 93 |
| 3 | | Methyl propionate | 72 | 50 | +5.1 (a) | 88 | +4.1 (b) | 91 |
| 4 | | Ethyl acetate | 72 | 52 | −1.52 (a) | 99 | +2.2 (a) | 92 |
| 5 | | Ethyl acetate | 120 | 48 | +13.9 (a) | 80 | −3.7 (d) | 82 |
| 6 | | Methyl propionate | 72 | 48 | +12.4 (c) | 94 | −5.4 (d) | 93 |

TABLE 1-continued

| Example | Substrate | Solvent | Time (h) | Conversion (%) | (R) Alcohol $[\alpha]_D^{20}$ | Recovery ⊖⊕ | (S) Ester $[\alpha]_D^{20}$ | Product ⊖⊕ |
|---|---|---|---|---|---|---|---|---|
| 7 | MeO-naphthyl-CH(CH₃)CH₂OH | Methyl propionate | 96 | 42 | +12.0 (c) | 66 | −12.0 (d) | 96 | a (as such)
b (C = 1, ethyl ether)
c (C = 1, CHCl)
d (C = 1, benzene)

TABLE 2

| Example | Substrate | Solvent | Time (h) | Conversion (%) | (R) Alcohol $[\alpha]_D^{20}$ | Recovery ⊖⊕ | (S) Ester $[\alpha]_D^{20}$ | Product ⊖⊕ |
|---|---|---|---|---|---|---|---|---|
| 9 | CH₃CH₂CH(CH₃)CH₂OH | Ethyl acetate | 72 | 50 | +5.4 (a) | 93 | +4.3 (b) | 93 |
| 10 | 2-ethylhexanol | Ethyl acetate | 96 | 51 | −1.51 (a) | 99 | +2.3 (a) | 96 |
| 11 | Ph-CH(CH₃)CH₂OH | Ethyl acetate | 120 | 50 | +13.9 (a) | 80 | −3.8 (d) | 84 |
| 12 | iBu-C₆H₄-CH(CH₃)CH₂OH | Methyl propionate | 72 | 48 | +12.4 (c) | 94 | −5.4 (d) | 93 |
| 13 | MeO-naphthyl-CH(CH₃)CH₂OH | Ethyl acetate | 96 | 43 | +12.2 (c) | 67 | −13.6 (d) | 95 | a (as such)
b (C = 1, ethyl ether)
c (C = 1, CHCl)
d (C = 1, benzene)

TABLE 3

| Example | Substrate | Solvent | Time (h) | Conversion (%) | (R) Alcohol $[\alpha]_D^{20}$ | Recovery ⊖⊕ | (S) Ester $[\alpha]_D^{20}$ | Product ⊖⊕ |
|---|---|---|---|---|---|---|---|---|
| 15 | CH₃CH₂CH(CH₃)CH₂OH | Ethyl acetate | 24 | 51 | +5.5 (a) | 95 | +4.3 (b) | 93 |
| 16 | 2-ethylhexanol | Methyl propionate | 24 | 50 | +1.52 (a) | 99 | +2.3 (a) | 96 |
| 17 | Ph-CH(CH₃)CH₂OH | Ethyl acetate | 40 | 60 | +7.0 (a) | 40 | −1.7 (d) | 37 |

TABLE 3-continued

| Example | Substrate | Solvent | Time (h) | Conversion (%) | (R) Alcohol $[\alpha]_D^{20}$ | Recovery ⊖⊕ | (S) Ester $[\alpha]_D^{20}$ | Product ⊖⊕ |
|---------|-----------|---------|----------|----------------|-------------------------------|-------------|-----------------------------|------------|
| 18 | MeO-naphthyl-CH(CH₃)-CH₂OH | Ethyl acetate | 40 | 56 | +5.6 (a) | 31 | −4.6 (d) | 32 | a (as such)
b (C = 1, ethyl ether)
c (C = 1, CHCl)
d (C = 1, benzene)

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. Process for the biotechnological separation, comprising enzymatic transesterification of the racemic mixture of the (S) and (R) optical isomers of the α-alkyl-substituted primary alcohols, having the formula (I):

$$\underset{R^i}{\underset{|}{R-CH-CH_2OH}} \quad (I)$$

wherein:

R represents a linear or branched ($C_1$-$C_{20}$)-alkyl or alkenyl group or an aryl group, a group of formula (II) or (III):

(II) phenyl with $R^{ii}$ and $R^{iii}$ substituents (III) naphthyl with $OR^{iv}$ substituent wherein:
$R^{ii}$ represents a ($C_1$-$C_8$)-alkyl group, a ($C_1$-$C_4$)-alkenyl group, an alkoxy, phenyl, phenoxy, benzoyl, heterocyclic group;
$R^{iii}$ represents a hydrogen or halogen atom;
$R^{iv}$ represents a ($C_1$-$C_4$)-alkyl group,
and wherein
$R^i$ represents a ($C_1$-$C_4$)-alkyl group different from R,
which process is characterized in that a racemic mixture of the α-alkyl-substituted primary alcohols of formula (I) is reacted with an ester having the formula (IV):

$$R^v-CO-O-R^{iv} \quad (IV)$$

wherein
$R^v$ and $R^{vi}$, which may be either equal to or different from each other, represent ($C_1$-$C_6$)-alkyl groups, at temperatures within the range of from 0° to 60° C., in the presence of an either free or immobilized enzyme capable of selectively causing the (S) isomer to be esterified, with the (R) isomer of the racemic starting compound of formula (I) being left substantially unchanged, said isomers then being separated from each other according to conventional techniques and wherein the enzyme is constituted by a lipase selected from the group consisting of lipase P from Pseudomonas fluorescens and Steapsin.

2. Process according to claim 1, wherein it is carried out with the use of an ester of a carboxy acid having formula (IV), in an amount in excess of the stoichiometric amount, said excess amount being within the range of from 10:1 to about 500:1 moles, relative to the alcohol of formula (I).

3. Process according to claim 2, wherein the ester of the carboxy acid of formula (IV) is used in an amount within the range of from 20:1 to about 100:1 moles, relative to the alcohol of formula (I).

4. Process according to claim 1, 2 or 3, wherein that the process is carried out at a temperature within the range of from 0° to about 60° C.

5. Process according to claim 4, wherein the process is carried out at a temperature within the range of from 20° to about 30° C.

6. Process according to the claims 1, 2 or 3, wherein ratios of enzyme/compound of formula (I) are used within the range of from 1:1 to about 1:100 by weight.

7. Process according to claim 1, wherein the ester of the carboxy acid of formula (IV) is selected from the class consisting of ethyl acetate, methyl propionate and methyl acetate.

8. Process according to claim 1, wherein the enzyme is supported on a porous support selected from the class consisting of celite, porous glass and silica.

* * * * *